United States Patent
Mailliet et al.

(10) Patent No.: US 6,645,964 B1
(45) Date of Patent: Nov. 11, 2003

(54) CHEMICAL DERIVATIVES AND THEIR APPLICATION AS ANTITELOMERASE AGENT

(75) Inventors: Patrick Mailliet, Fontenay Sous Bois (FR); Jean-François Riou, Paris (FR); Jean-Louis Mergny, Villejuif (FR); Abdelazize Laoui, Nogent sur Marne (FR); François Lavelle, Paris (FR); Odile Petitgenet, Paris (FR)

(73) Assignee: Aventis Pharma S.A., Atony (FR)

( * ) Notice: Subject to any disclaimer, the term of this patent is extended or adjusted under 35 U.S.C. 154(b) by 0 days.

(21) Appl. No.: 09/722,361

(22) Filed: Nov. 28, 2000

Related U.S. Application Data

(60) Provisional application No. 60/218,059, filed on Jul. 13, 2000, and provisional application No. 60/176,632, filed on Jan. 19, 2000.

(30) Foreign Application Priority Data

Nov. 29, 1999 (FR) ............................................. 99 15031
Aug. 11, 2000 (FR) ............................................. 00 10561

(51) Int. Cl.[7] ....................... A61K 31/53; C07D 251/18; C07D 251/54
(52) U.S. Cl. ........................ 514/245; 544/197; 544/198; 544/208; 544/209
(58) Field of Search ................................. 544/197, 198, 544/208, 209; 514/245

(56) References Cited

PUBLICATIONS

Gill , Chemical Abstracts, vol. 76:94467, 1972.*
Burton et al., Chemical Abstracts, vol. 118:96775, 1993.*

* cited by examiner

*Primary Examiner*—Richard L. Raymond
(74) *Attorney, Agent, or Firm*—Finnegan, Henderson, Farabow, Garrett & Dunner LLP

(57) ABSTRACT

The present invention relates to cancer therapy and to novel anticancer agent having a mechanism of action which is quite specific. It also relates to novel chemical compounds as well as their therapeutic application in humans.

19 Claims, No Drawings

CHEMICAL DERIVATIVES AND THEIR APPLICATION AS ANTITELOMERASE AGENT

This application claims the benefit of provisional application No. 60/176,632, filed Jan. 19, 2000, and provisional application No. 60/218,059, filed Jul. 13, 2000, and the right to priority based on French Application No. 9915031, filed Nov. 29,1999, and French Application No. 00 10561, filed Aug. 11, 2000, the contents of each of which is incorporated herein by reference.

The present invention relates to cancer therapy and to novel anticancer agents having a mechanism of action which is quite specific. It also relates to novel chemical compounds as well as their therapeutic application in humans.

The present invention relates to the use of novel non-nucleotide chemical compounds which interact with specific structures of deoxyribonucleic acid (DNA). These novel compounds consist of a distribution agent linked to two aminoaromatic groups. These novel compounds are useful in the treatment of cancers and act in particular as telomerase-inhibiting agents. They are particularly useful for stabilizing DNA in G-quadruplex structure (guanine tetrads). The therapeutic application of the inhibition of telomerase via the stabilization of these G-quadruplexes is the termination of cellular mitosis and the death of rapidly dividing cells such as cancer cells and possibly the induction of the senescence of cancer cells.

The compounds of the present invention have the advantage, from the therapeutic point of view, of blocking telomerase. From a biological point of view, telomerase allows the addition of repetitive DNA sequences of the TTAGGG type, termed telomeric sequences, at the end of the telomer, during cell division. Through this action, telomerase renders the cell immortal. Indeed, in the absence of this enzymatic activity, the cell loses, at each division, 100 to 150 bases, which rapidly renders it senescent. During the appearance of rapidly dividing cancer cells, it appeared that these cells possessed telomers which were maintained at a stable length during cell division. In these cancer cells, it appeared that telomerase was highly activated and that it allowed the addition of repetitive motifs of telomeric sequences at the end of the telomer and therefore allowed conservation of the length of the telomer in the cancer cells. It appeared for some time that more than 85% of cancer cells showed positive tests for the presence of telomerase whereas somatic cells do not show this characteristic.

Thus, telomerase is a highly coveted target for treating cancer cells. The first obvious approach for blocking telomerase was the use of nucleotide structures (Chen et al., Proc. Natl. Acad. Sci. USA 93(7), 2635–2639). Among the non-nucleotide compounds which have been used in the prior art, there may be mentioned the diaminoanthraquinones (Sun et al., J. Med. Chem. 40(14), 2113–6) or the diethyloxadicarbocyanins (Wheelhouse R. T. et al., J. Am. Chem. Soc. 1998(120), 3261–2).

Patent WO 99/40087 describes the use of compounds which interact with the G-quadruplex structures which are perylene compounds and carbocyanins containing at least seven rings including two heterocycles.

It appeared, quite surprisingly, that simple structures made it possible to obtain a result which is at least equivalent with structures which are a lot less complicated from a chemical point of view. The compounds of the present invention which meet the intended objective, that is to say which bind the G-quadruplex structure and thereby exhibit a telomerase-inhibiting activity, correspond to the following general formula:

nitrogen-containing aromatic ring—$NR_3$—distribution agent—$NR'_3$—aromatic ring in which the nitrogen-containing aromatic ring represents:
- a quinoline optionally substituted with at least one group N(Ra)(Rb) in which Ra and Rb, which are identical or different, represent hydrogen or a short-chain C1–C4 alkyl and/or alkoxy radical and/or
- a quinoline possessing a nitrogen atom in quaternary form or
- a benzamidine or
- a pyridine the aromatic ring represents
- a quinoline optionally substituted with at least one group N(Ra)(Rb) in which Ra and Rb, which are identical or different, represent hydrogen or a short-chain C1–C4 alkyl and/or alkoxy radical and/or
- a quinoline possessing a nitrogen atom in quaternary form or
- a benzamidine or
- a pyridine or
- a phenyl ring optionally substituted at the meta or para position with a halogen group, C1–C4 alkoxy group, cyano group, carbonylamino group optionally substituted with one or more C1–C4 alkyl groups, guanyl groups, C1–C4 alkylthio groups, amino groups, C1–C4 alkylamino groups, C1–C4 dialkylamino groups for each alkyl group, nitro group, alkylene-amino group or alkenyleneamino group or
- a mono- or bi- or tricyclic hetero-cyclic ring comprising 0 to 2 heteroatoms per ring provided that at least one heteroatom is present in at least one ring optionally substituted with one or more C1–C4 alkyl groups or with alkylene or alkenylene groups R3 and R'3, which are identical or different, represent independently of one another hydrogen or a C1–C4 alkyl radical the distribution agent represents:
- a triazine group optionally substituted with an alkyl radical having 1 to 4 carbon atoms, a thio, oxy or amino radical which are themselves optionally substituted with one or more short-chain alkyl chains containing 1 to 4 carbon atoms or a halogen atom or
- a carbonyl group or
- a group C(=NH)—NH—C(=NH) or
- an alkyldiyl group containing 3 to 7 carbon atoms or
- a diazine group optionally substituted with the same groups as the triazine or one of its salts.

For the purposes of the above formula, nitrogen-containing aromatic ring is understood to mean a heterocycle comprising at least one nitrogen atom or an aromatic group containing no heteroatom in the ring but containing at least one nitrogen atom in a hydrocarbon chain attached to the ring, such as for example a guanidino or guanyl chain.

Among all the compounds included above, the use of those comprising, as distribution agent, a triazine or diazine group is preferred. Among the diazine groups, the use of pyrimidines is preferred. Among the triazines, those preferred are the compounds corresponding to formula (I) below:

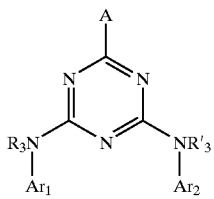

in which:
A represents
an amino group of formula NR1R2 in which R1 and R2, which are identical or different, represent hydrogen or a straight or branched alkyl group containing 1 to 4 carbon atoms or
a group OR1 or SR1 in which R1 has the same meaning as above or
an alkyl group containing 1 to 4 carbon atoms or a trifluoromethyl group or
a hydrogen atom or
a halogen atom chosen from fluorine, chlorine, bromine or iodine
R3 and R'3, which are identical or different, represent independently of one another hydrogen or a C1–C4 alkyl radical
$Ar_1$ and $Ar_2$, which are identical or different, represent
1. when $Ar_1$ and $Ar_2$ are identical:
a quinoline motif optionally substituted with at least one group N(Ra)(Rb) in which Ra and Rb, which are identical or different, represent hydrogen or a short-chain alkyl and/or alkoxy radical containing 1 to 4 carbon atoms or
a quinoline possessing a nitrogen atom in quaternary form or
a benzamidine or
a pyridine attached at the 4-position or fused with an aryl or heteroaryl group optionally substituted with a C1–C4 alkyl group
2. when $Ar_1$ and $Ar_2$ are different
$Ar_1$ and $Ar_2$ both represent one of the possibilities mentioned above for $Ar_1$ and $Ar_2$ or
$Ar_1$ represents one of the above possibilities and $Ar_2$ represents
a phenyl ring optionally substituted at the meta or para position with a halogen group, C1–C4 alkoxy group, cyano group, carbonylamino group optionally substituted with one or more C1–C4 alkyl groups, guanyl groups, C1–C4 alkylthio groups, amino groups, C1–C4 alkylamino groups, C1–C4 dialkylamino groups for each alkyl group, nitro group, alkyleneamino group or alkenyleneamino group
a mono- or bi- or tricyclic hetero-cyclic ring comprising 0 to 2 heteroatoms per ring provided that at least one heteroatom is present in at least one ring optionally substituted with one or more C1–C4 alkyl groups or with alkylene or alkenylene groups
or one of its salts.

It is evident that the quinoline motifs may be substituted by any other group not involved in the intended application; thus, acridine or isoquinoline or quinazoline or quinoxaline or phthalazine or benzothiazine or benzoxazine or phenoxazine or phenothiazine groups are included in the definition of the quinoline groups.

Among the above compounds of formula (I), there are preferred those comprising two heterocycles chosen from the 4-aminoquinolyl, 4-aminoquinolinium or quinolinium groups in which the quinolinium ring is optionally substituted with a methyl group.

As regards the R1 and R2 groups, they preferably represent the methylthio, amino, alkylamino or dialkylamino radical, in which radicals the alkyl groups possess 1 to 4 carbon atoms.

The following compounds may be mentioned by way of representative compounds of formula (I):

2-amino-bis-4,6-[(1'-methyl-4'-amino-6'-quinaldinio)amino]triazine dichloride 2-amino-bis-4,6-[(1'-ethyl-4'-amino-6'-quinaldinio)amino]triazine dichloride 2-dimethylamino-bis-4,6-[(1'-methyl-4'-amino-6'-quinaldinio)amino]triazine dichloride 2-methylamino-bis-4,6-[(4'-amino-6'-quinaldinyl)amino]triazine trihydrochloride 2-amino-bis-4,6-[(1'-methyl-6'-quinolinio)-amino]triazine dichloride 2-methylamino-bis-4,6-[(4'-methylamino-6'-quinaldinyl)amino]triazine dichloride trihydrochloride 2-amino-bis-4,6-[(9'-amino-10'-methyl-2'-acridinio)amino)triazine dichloride hydrochloride 2-amino-bis-4,6-[(4'-amino-6'-quinaldinyl)-amino]triazine trihydrochloride 2-amino-bis-4,6-(p-amidinoanilino)triazine trihydrochloride 2-methylthio-bis-4,6-[(1'-methyl-4'-amino-6'-quinaldinio)amino]triazine dichloride 2-chloro-bis-4,6-[(4'-dimethylamino-6'-quinaldinyl)amino]triazine dihydrochloride dihydrate 2-methylthio-bis-4,6-[(4'-dimethylamino-6'-quinaldinyl)amino]triazine hydrate N,N'-(4-amino-6-quinaldinyl)urea dihydrochloride $N^1,N^5$-bis(7-chloro-1-methyl-4-quinolinio)-pentane-1,5-diamine diiodide bis-2,4-[(4'-amino-6'-quinaldinyl)amino]-pyrimidine trihydrochloride pentahydrate 1,5-(4'-amino-6'-quinaldinyl)biguanide trihydrochloride dihydrate 6-[4-(4-amino-2-methylquinolin-6-ylamino)-6-methylsulphanyl-[1,3,5]triazin-2-ylamino]-2-methyl-quinolin-4-ol N6-[4-(4-dimethylamino-2-methylquinolin-6-ylamino)-6-methylsulphanyl-[1,3,5]triazin-2-yl]-2-methylquinoline-4,6-diamine N6-[4-(4-amino-2-methylquinolin-6-ylamino)-6-methylsulphanyl-[1,3,5]triazin-2-yl]-2-methylquinoline-4,6-diamine N6-[4-(4-methoxy-2-methylquinolin-6-ylamino)-6-methylsulphanyl-[1,3,5]triazin-2-yl]-4-methoxy-2-methylquinolin-6-amine Another subject of the present invention relates to the compounds of formula (I) as novel chemical products. It therefore relates to the novel products corresponding to the following formula (I):

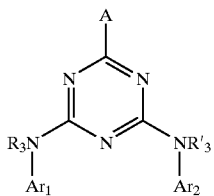

in which:

A represents
- an amino group of formula NR1R2 in which R1 and R2, which are identical or different, represent a straight or branched alkyl group containing 1 to 4 carbon atoms or
- a group OR1 or SR1 in which R1 represents hydrogen or has the same meaning as above or
- an alkyl group containing 1 to 4 carbon atoms or a trifluoromethyl group or
- a hydrogen atom or
- a halogen atom chosen from fluorine, chlorine, bromine or iodine $R_3$ and $R'_3$, which are identical or different, represent independently of one another a hydrogen atom or a C1–C4 alkyl group $Ar_1$ and $Ar_2$, which are identical or different, represent
1. when Ar, and $Ar_2$ are identical:
   - a quinoline motif optionally substituted with at least one group N(Ra)(Rb) in which Ra and Rb, which are identical or different, represent hydrogen or a short-chain alkyl and/or alkoxy radical containing 1 to 4 carbon atoms and/or
   - a quinoline possessing a nitrogen atom in quaternary form or
   - a benzamidine except in the case where A represents diethylamine, hydrogen or an amine group
   - a pyridine attached at the 4-position or fused with an aryl or heteroaryl group optionally substituted with a C1–C4 alkyl group
2. when $Ar_1$ and $Ar_2$ are different
   - $Ar_1$ and $Ar_2$ both represent one of the possibilities mentioned above for $Ar_1$ and $Ar_2$ or
   - $Ar_1$ represents one of the above possibilities and $Ar_2$ represents
     - a phenyl ring optionally substituted at the meta or para position with a halogen group, C1–C4 alkoxy group, cyano group, carbonylamino group optionally substituted with one or more C1–C4 alkyl groups, guanyl groups, C1–C4 alkylthio groups, amino groups, C1–C4 alkylamino groups, C1–C4 dialkylamino groups for each alkyl group, nitro group, alkyleneamino group or alkenyleneamino group
     - a mono- or bi- or tricyclic hetero-cyclic ring comprising 0 to 2 heteroatoms per ring provided that at least one heteroatom is present in at least one ring optionally substituted with one or more C1–C4 alkyl groups or with alkylene or alkenylene groups or one of its salts excluding 2-amino-bis-4,6-[(4'-amino-6'-quinaldinyl)amino]triazine dihydrochloride and 2-amino-bis-4,6-(p-amidinoanilino)triazine dihydrochloride.

Indeed, the first of these two compounds is described in a publication which appeared under the reference Indian Journal of Animal Sciences 43 (4), pages 226–29, as antitrypanosome agent for animals and in no case as antitelomerase agent and the second compound is also described as antitrypanosome agent in J. Chem. Soc., 1960, 4525.

The compounds of formula (I) which are preferred are those for which $Ar_1$ and $Ar_2$ represent a group chosen from the following motifs: 4-amino- or 4-methylamino- or 4-dimethylamino-quinolyl or quinolinium in which the quinolinium ring is optionally substituted with a methyl group.

The compounds of general formula (I) which are preferred are those for which A represents an amino or dimethylamino or, more preferably, methylthio group.

There are most particularly preferred the compounds of formula (I) for which when $Ar_1$ and $Ar_2$ are different:
1. $Ar_1$ represents:
   - a quinoline motif substituted with at least one group N(Ra)(Rb) in which Ra and Rb, which are identical or different, represent hydrogen or a short-chain alkyl or alkoxy radical containing 1 to 4 carbon atoms and/or
   - a quinoline possessing a nitrogen atom in quaternary form or
   - a benzamidine except in the case where A represents diethylamine, hydrogen or an amine group or
   - a pyridine attached at the 4-position or fused with an aryl or heteroaryl group
2. $Ar_2$ represents
   - a ring as defined above but different or
   - a phenyl ring optionally substituted at the meta or para position with a halogen, methoxy, cyano, carbonylamino, guanyl, methylthio, amino, methylamino, dimethylamino, morpholine, alkyleneamino or alkenyleneamino group
   - a quinoline, benzimidazole, indole, benzothiophene, benzofuran, benzothiazol, benzoxazol, carbazol, quinazoline or quinoxaline ring optionally substituted with one or more C1–C4 alkyl groups or with alkylene or alkenylene groups or one of its salts excluding 2-amino-bis-4,6-[(4'-amino-6'-quinaldinyl)amino]triazine dihydro-chloride and 2-amino-bis-4,6-(p-amidinoanilino)-triazine.

Another subject of the present invention relates to the use of the compounds of formula (I) as pharmaceutical product for human use.

The methods of preparing the compounds of formula (I)

(I)

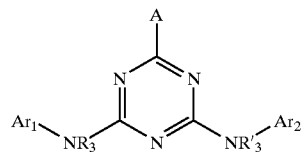

are described below.

General Method 1

According to a first preparation method, compounds of general formula (I) in which $Ar_1$ and $Ar_2$ are identical and defined as above and R represents a halogen atom such as chlorine or fluorine, an amino, alkylamino or dialkylamino function in which the straight or branched alkyl portions contain from 1 to 4 carbon atoms, an alkyloxy or alkylthio function in which the straight or branched alkyl portions contain from 1 to 4 carbon atoms, may be obtained by amination of a dihalotriazine, most generally a dichloro-s-triazine, of general formula (B) in which A is as defined above, with an aromatic or heteroaromatic amine of general formula (C) in which Ar is as defined above, the procedure being carried out according to scheme 1:

Scheme 1

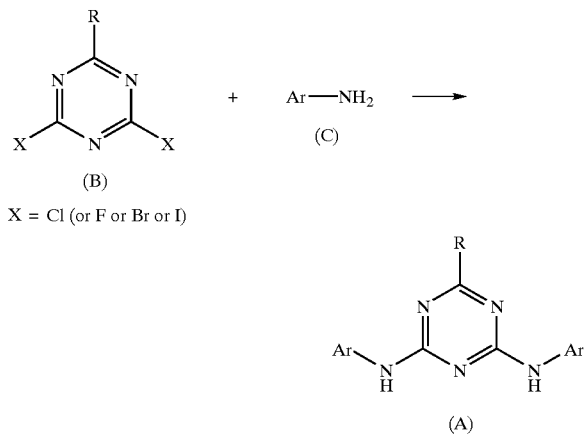

In the case where A represents a halogen atom, it is useful to react the corresponding 2,4,6-trihalo-s-triazine of general formula (B) with the aromatic or heteroaromatic amine ArNH₂ of general formula (C).

The procedure is generally carried out by condensing one mole of dihalo-s-triazine, or trihalo-s-triazine, with 2 moles of aromatic or heteroaromatic amine. The reaction takes place in an inert medium under the reaction conditions. There may be mentioned, among the inert solvents, acetone which is optionally aqueous or an alcohol which is optionally aqueous such as ethanol, or a halogenated solvent such as dichloromethane, or an ether such as diethyl ether or dioxane, or a polar aprotic solvent such as DMF, DMSO or NMP. The procedure is preferably carried out at a temperature of between 20° C. and the reflux temperature, in the presence in particular of an organic base such as triethylamine, or an inorganic base such as sodium hydroxide or sodium or potassium carbonate. It is also possible not to use a base during the amination reaction, and to isolate a hydrochloride of the product of general formula (A), whose base can then be released.

The dihalo- or trihalo-s-triazines of general formula (B) are either commercially available or are known, and may be obtained under the conditions described in the literature.

The aromatic or heteroaromatic amines of general formula (C) are either known or may be easily prepared by the known methods of synthesizing aromatic or heteroaromatic amines.

In the case where $Ar_1$ and Ar2 are different, the triazine of general formula (A) may be obtained by sequential displacement of the halogen atoms, most generally of the chlorine atoms, from the products of general formula (B) by the amines $Ar_1$ and then $Ar_2$ of general formula (C) according to scheme 2:

Scheme 2

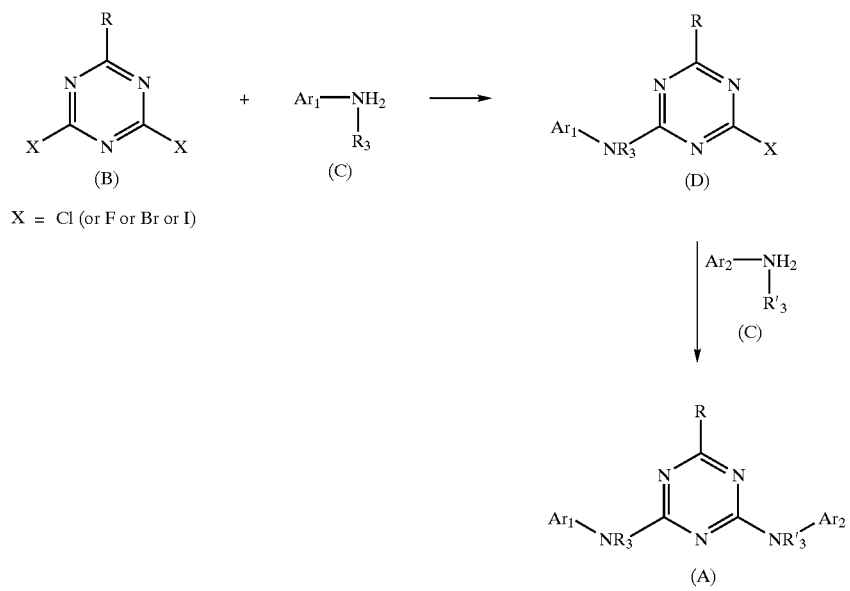

Generally, the procedure is carried out with 1 mole of dihalo-s-triazine, or trihalo-s-triazine, and 1 mole of amine $Ar_1$. The procedure is preferably carried out in an inert solvent such as acetone which is optionally aqueous or an alcohol which is optionally aqueous, such as ethanol, or a halogenated solvent such as dichloromethane, or an ether such as diethyl ether or dioxane, or a polar aprotic solvent such as DMF, DMSO or NMP. According to a better way of carrying out the invention, the procedure is carried out at a temperature of between 20° C. and 50° C. Next, 1 mole of amine $Ar_2$ is added to the product of general formula (D), which may be optionally isolated. The procedure is carried out in particular at a temperature of between 50° C. and the reflux temperature.

Advantageously, it is possible to carry out the procedure under the conditions described in J. Fluor. Chem., 1988, 39(1), 117–123.

General Method 2

According to a second method, the products of general formula (A) in which Ar are as defined above and R represents a group NR1R2 or OR1 or SR1 may also be prepared by nucleophilic displacement of a halogen atom, generally a chlorine atom, from a product of general formula (A) in which R represents a halogen atom according to scheme 3:

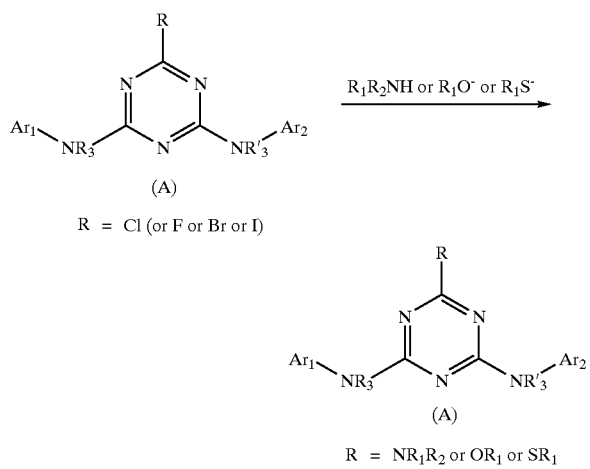

The procedure is generally carried out by condensing 1 mole of product of general formula (A) in which R represents a halogen atom, preferably a chlorine atom, with 1 mole of amine R1R2NH or alcoholate R1O$^-$ or thioalcoholate R1S$^-$. The reaction takes place in an inert medium under the reaction conditions. There may be mentioned among the inert solvents acetone which is optionally aqueous or an alcohol which is optionally aqueous such as ethanol, or a halogenated solvent such as dichloromethane, or an ether such as diethyl ether or dioxane, or a polar aprotic solvent such as DMF, DMSO or NMP. When the entering group represents a group R1R2NH, the procedure is preferably carried out at a temperature of between 20° C. and the reflux temperature, in the presence in particular of an organic base such as triethylamine, or an inorganic base such as sodium hydroxide or sodium or potassium carbonate. It is also possible not to use a base during the amination reaction, and to isolate a hydrochloride of the product of general formula (A), the base of which can then be released. When the entering group represents a group R10$^-$ or R1S$^-$, the procedure is preferably carried out with an alkali metal or alkaline-earth metal alcoholate or thioalcoholate, such as a sodium or potassium or lithium or ammonium or caesium or barium salt, in a polar aprotic solvent such as DMF or DMSO or NMP, at a temperature of between 50° C. and the reflux temperature.

General Method 3

According to a third preparation method, the compounds for which R represents a hydrogen atom or a straight or branched alkyl group containing from 1 to 4 carbon atoms may also be prepared by condensation of a bisguanide of general formula (E), in which $Ar_1$ and $Ar_2$ are identical or different, with an acid derivative, preferably an acid chloride or a methyl ester of general formula (F) according to scheme 4:

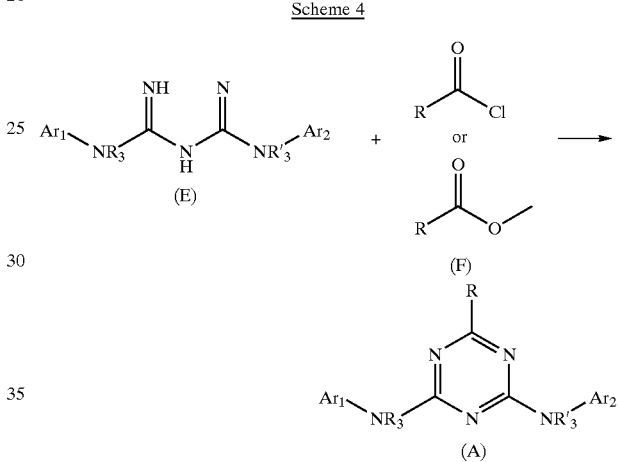

The condensation between the bisguanide of general formula (E) and the acid derivative of general formula (F) is generally carried out in an alcohol such as methanol or ethanol. The procedure is preferably carried out at a temperature of between 0° C. and the reflux temperature.

The symmetric or asymmetric bisguanides of general formula (E) may be obtained by carrying out the procedure under the conditions described in the literature and in particular according to Patent J.P. 94-4993.

General Method 4

The products of general formula (A), in which $Ar_1$ and $Ar_2$ are identical, as defined above and represented by Ar, and where R represents a straight or branched alkyl group containing from 1 to 4 carbon atoms, may also be prepared by condensation of a cyanoguanidine of general formula (G), in which Ar is as defined above, with a nitrile of general formula (H) according to scheme 4:

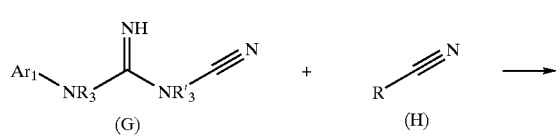

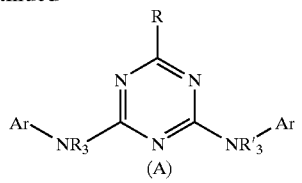

(A)

The condensation of the cyanoguanidine of general formula (G) with the nitrile of general formula (H) is in particular performed by carrying out the procedure at the reflux temperature of a polar solvent with a high boiling point such as 2-methoxyethanol or 1,2-dimethoxyethane.

The cyanoguanidines of general formula (G) may be prepared under the conditions described in the literature.

It is understood that the s-triazines of general formula may be obtained in the form of libraries, by applying the methods described in schemes 1, 2, 3, 4 or 5 in parallel and/or combinatorial chemistry in liquid phase or in solid phase, it being understood that when the work is carried out in solid phase, any of the reagents is attached beforehand onto a solid support, chosen according to the chemical reaction involved, and that said chemical reaction is followed by an operation of cleaving the product of the reaction from the solid support.

The present invention also relates to therapeutic compositions containing a compound according to the invention, in combination with a pharmaceutically acceptable carrier according to the mode of administration chosen. The pharmaceutical composition may be provided in solid, liquid or liposome form.

Among the solid compositions, there may be mentioned powders, gelatin capsules and tablets. Among the oral forms, it is also possible to include the solid forms which are protected from the acidic medium of the stomach. The carriers used for the solid forms consist in particular of inorganic carriers such as phosphates, carbonates or organic carriers such as lactose, celluloses, starch or polymers. The liquid forms consist of solutions, suspensions or dispersions. They contain, as dispersive carrier, either water or an organic solvent (ethanol, NMP and the like) or mixtures of surfactants and solvents or of complexing agents and solvents.

The administered dose of the compounds of the invention will be adjusted by the practitioner according to the route of administration, the patient and the condition of the latter.

The compounds of the present invention may be administered alone or mixed with other anticancer agents. Among the possible combinations, there may be mentioned alkylating agents and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as in particular cisplatin, carboplatin or oxaliplatin antibiotic agents such as in particular bleomycin, mitomycin, dactinomycin, antimicrotubule agents such as in particular vinblastine, vincristine, vindesine, vinorelbine, taxoids (paclitaxel and docetaxel)

anthracyclines such as in particular doxorubicin, daunorubicin, idarubicin, epirubicin, mitoxantrone, losoxantrone group I and II topoisomerases such as etoposide, teniposide, amsacrine, irinotecan, topotecan and tomudex, fluoropyrimidines such as 5-fluorouracil, UFT, floxuridine, cytidine analogues such as 5-azacytidine, cytarabine, gemcitabine, 6-mercaptomurine, 6-thioguanine adenosine analogues such as pentostatin, cytarabine or fludarabine phosphate methotrexate and folinic acid various enzymes and compounds such as L-asparaginase, hydroxyurea, trans-retinoic acid, suramine, dexrazoxane, amifostine, herceptin as well as oestrogenic and androgenic hormones.

It is also possible to combine a radiation treatment with the compounds of the present invention. This treatment may be administered simultaneously, separately or sequentially. The treatment will be adapted to the patient to be treated by the practitioner.

The G-quadruplex stabilizing activity may be determined by a method using the formation of a complex with fluorescein of which the experimental protocol is described below.

Oligonucleotides

All the nucleotides, modified or otherwise, were synthesized by Eurogentec SA, Seraing, Belgium. The oligonucleotide FAM+DABCYL carries the catalogue reference OL-0371-0802. It has the sequence: GGGTTAGGGT-TAGGGTTAGGG corresponding to 3.5 repeats of the human telomeric motif (strand rich in G). The fluorescein is attached to the 5' end, the DABCYL to the 3' end, by the chemical arms described by Eurogentec. The concentration of the samples is checked by spectrophotometry, recording the absorbance spectrum between 220 and 700 nm and using the molar extinction coefficient provided by the supplier.

Buffers

All the experiments were carried out in a 10 mM sodium cacodylate buffer pH 7.6 containing 0.1 M lithium chloride (or sodium chloride). The absence of fluorescent contamination in the buffer was checked beforehand. The fluorescent oligonucleotide is added at the final concentration of 0.2 $\mu$M.

Study of Fluorescence

All the measurements of fluorescence were carried out on a Spex Fluorolog DM1B apparatus, using an excitation line width of 1.8 nm and an emission line width of 4.5 nm. The samples are placed in a microquartz cuvette of 0.2×1 cm. The temperature of the sample is controlled by an external water bath. The oligonucleotide alone was analysed at 20, 30, 40, 50, 60, 70 and 80° C. The emission spectra are recorded using an excitation wavelength of 470 nm. The excitation spectra are recorded using either 515 nm or 588 nm as emission wavelength. The spectra are corrected for the response of the instrument by reference curves. A high extinction (80–90%) of the fluorescence of fluorescein at room temperature is observed, in agreement with an intramolecular folding of the oligonucleotide at 20° C. in the form of a G-quadruplex, which induces juxtaposition of its 5' and 3' ends which are respectively linked to fluorescein and to DABCYL. This juxtaposition causes an already-described phenomenon of extinction of fluorescence which is used for "molecular beacons".

Fluorescence Tm

An oligonucleotide stock solution at the strand concentration of 0.2 $\mu$M in 0.1 M LiCl, 10 mM cacodylate buffer, pH 7.6, is prepared beforehand, heated briefly at 90° C. and slowly cooled to 20° C., and then distributed in aliquots of 600 μl in the fluorescence cuvettes. 3 μl of water (for the control) or 3 μl of test product (stock at 200 μM, final concentration 1 μM) are then added and mixed. The samples are then allowed to incubate for at least 1 hour at 20° C. before each measurement. The use of longer incubation times (up to 24 hours) has no influence on the result obtained.

Each experiment allows the measurement of only one sample. The latter is first incubated at an initial temperature of 20° C., heated to 80° C. over 38 minutes, left for 5 minutes at 80° C. and then cooled to 20° C. over 62 minutes. During this time, the fluorescence is measured simultaneously at two emission wavelengths (515 nm and 588 nm) using 470 nm as excitation wavelength. A measurement is carried out every 30 seconds. The temperature of the water bath is recorded in parallel, and the fluorescence profile as a function of the temperature is reconstituted from these values. The fluorescence profiles are then normalized between 20° C. and 80° C., and the temperature for which the intensity of emission at 515 nm is the mean of those at high and low temperature is called Tm. Under these conditions, the Tm of the reference sample without addition of product is 44° C. in a lithium chloride buffer. This temperature is increased to more than 55° C. in a sodium chloride buffer. The addition of a G-quadruplex-stabilizing compound induces an increase in the Tm. This increase is judged to be significant if it is greater than 3°.

The antitelomerase biological activity is determined by the following experimental protocol:

Preparation of the Extract Enriched in Human Telomerase Activity

The leukaemia line HL60 is obtained from ATCC (American Type Culture Collection, Rockville, USA). The cells are cultured in suspension in RPMI 1640 medium containing L-glutamine at 2 mM, penicillin 200 U/ml, streptomycin 200 μg/ml, gentamycin 50 μg/ml and supplemented with 10% heat-inactivated foetal calf serum.

An aliquot of $10^5$ cells is centrifuged at 3000×G and the supernatant discarded. The cell pellet is resuspended by several successive pipettings in 200 μl of lysis buffer containing 0.5% CHAPS, 10 mM Tris-HCl, pH 7.5, 1 mM $MgCl_2$, 1 mM EGTA, 5 mM β-mercaptoethanol, 0.1 mM PMSF and 10% glycerol and is stored in ice for 30 minutes. The lysate is centrifuged at 160,000×G for 20 minutes at 4° C. and 160 μl of supernatant are recovered. The proteins in the extract are assayed by the Bradford method. The extract is stored at −80° C.

Assay of the Telomerase Activity

The inhibition of the telomerase activity is determined by a protocol for extension of the oligonucleotide TS ($5'$ AATCGTTCGAGCAGAGTT$^{3'}$), in the presence of a cellular extract enriched in telomerase activity and compounds which are added at various concentrations (10, 1, 0.1 and 0.01 μg/ml). The extension reaction is followed by a PCR amplification of the extension products with the aid of the oligonucleotides TS and CXext ($5'$ GTGCC-CTTACCCTTACCCTTACCCTAA$^{3'}$).

The reaction medium is prepared based on the following composition:

| | |
|---|---|
| Tris HCl pH 8.3 | 20 mM |
| MgCl2 | 1.5 mM |
| Tween 20 | 0.005% (P/V) |
| EGTA | 1 mM |
| dATP | 50 μM |
| dGTP | 50 μM |
| dCTP | 50 μM |
| dTTP | 50 μM |
| Oligonucleotide TS | 2 μg/ml |
| Oligonucleotide CXext | 2 μg/ml |
| Bovine serum albumin | 0.1 mg/ml |
| Taq DNA polymerase | 1 U/ml |
| alpha 32P dCTP (3000 Ci/mmol) | 0.5 μl |
| Telomerase extract | 200 ng in a volume of 10 μl |
| Test product or solvent | in a volume of 5 μl |

Double-distilled water QS . . . 50 μl

The oligonucleotides are obtained from Eurogentec (Belgium) and are stored at −20° C. at a stock concentration of 1 mg/ml in distilled water.

The reaction samples are assembled in 0.2 ml PCR tubes and one drop of paraffin oil is deposited on each of the reactions of the experiment before closing the tubes.

The reaction samples are then incubated in a Cetus 4800-type PCR apparatus under the following temperature conditions:

15 minutes at 30° C.,
1 minute at 90° C.,
followed by 30 cycles of,
30 seconds at 94° C.,
30 seconds at 50° C.,
and 1 minute 30 seconds at 72° C.,
followed by a final cycle of 2 minutes at 72° C.

For each of the samples, an aliquot of 10 μl is pipetted under the oil layer and mixed with 5 μl of a loading buffer containing:

| | |
|---|---|
| TBE | 3X |
| glycerol | 32% (P/V) |
| bromophenol blue | 0.03% |
| xylene cyanol | 0.03% |

The samples are then analysed by electrophoresis on 12% acrylamide gel in a 1×TBE buffer for 1 hour at a voltage of 200 volts, with the aid of a Novex electrophoresis system.

The acrylamide gels are then dried on a sheet of whatmann 3MM paper at 80° C. for 1 hour.

The analysis and the quantification of the reaction products are carried out with the aid of an InstantImager apparatus (Pacard).

For each compound concentration tested, the results are expressed as percentage inhibition of the reaction and calculated from the untreated enzymatic control and from the enzyme-free sample (blank) according to the following formula:

(compound value−blank value/enzymatic control value−blank value)×100.

The concentration of compound inducing a 50% inhibition of the telomerase reaction (IC50) is determined with the aid of a semilogarithmic graphical representation of the inhibition values obtained as a function of each of the compound concentrations tested.

A compound is considered to be active as an antitelomerase agent when the quantity inhibiting 50% of the telomerase reaction is in particular less than 5 μM.

The Cytotoxic Biological Activity on Human Tumour Lines is Determined According to the Following Experimental Protocol The human cell lines KB and A549 are obtained from ATCC (American Type Culture Collection, Rockville, USA). The A549 cells are cultured in a layer in a culture flask in RPMI 1640 medium containing L-glutamine at 2 mM, penicillin 200 U/ml, streptomycin 200 µg/ml and supplemented with 10% heat-inactivated foetal calf serum. The KB cells are cultured in a layer in a culture flask in Dulbelco's medium containing L-glutamine at 2 mM, penicillin 200 U/ml, streptomycin 200 µg/ml and supplemented with 10% heat-inactivated foetal calf serum.

The cells at the exponential growth phase are trypsinized, washed in 1×PBS and are inoculated in 96-well microplates (Costar) in an amount of 4×10$^4$ cells/ml for A549 and of 1.5×10$^4$ cells/ml (0.2 ml/well) and then incubated for 96 hours in the presence of variable concentrations of product to be studied (10, 1, 0.1 and 0.01 µg/ml, each point in quadruplicate). 16 hours before the end of the incubation, 0.02% final of neutral red is added to each well. At the end of the incubation, the cells are washed with 1×PBS and lysed with 1% sodium lauryl sulphate. The cellular incorporation of the dye, which reflects cellular growth, is evaluated by spectrophotometry at a wavelength of 540 nm for each sample with the aid of a Dynatech MR5000 reading apparatus.

For each compound concentration tested, the results are expressed as percentage inhibition of cellular growth and calculated from the untreated control and the culture medium free of cells (blank) according to the following formula:

(compound value−blank value/cell control value−blank value)×100.

The concentration of compound inducing a 50% inhibition of growth (IC50) is determined with the aid of a semilogarithmic graphical representation of the inhibition values obtained as a function of each of the compound concentrations tested.

A compound is considered to be active as cytotoxic agent if the concentration inhibiting the growth of the tumour cells tested by 50% is in particular less than 10 µM.

The following non-limiting examples are given to illustrate the invention.

EXAMPLE 1

Preparation of 2-Amino-bis-4,6-((1'-methyl-4'-amino-6'-quinaldinio)amino]triazine Dichloride 200 cm$^3$ of distilled water are introduced into a 2-dm$^3$ three-necked flask and 41.6 g (0.16 mol) of 1-methyl-4,6-diaminoquinaldinium chloride hydrochloride, which may be obtained according to J. Chem. Soc., 1953, 50, are loaded, with stirring. A clear dark yellow solution is obtained into which 800 cm$^3$ of ethanol are poured, causing an abundant precipitate. The mixture is heated to 45° C. to dissolve, and then 13.2 g (0.08 mol) of 2-amino-4,6-dichlorotriazine, which may be prepared according to J. Amer. Chem. Soc., 1945, 67, 662, are added. After a few minutes, a yellow precipitate appears, and the mixture is heated under reflux for 1 hour. The mixture is cooled and left overnight on an ice bath. The precipitate obtained is filtered and washed with four times 100 cm$^3$ of 80% aqueous ethanol and then dried at 45° C. 47 g (100%) of 2-amino-bis-4,6-[(1'-methyl-4'-amino-6'-quinaldinio)amino]triazine dichloride monohydrochloride are thus obtained.

Release and Purification of the Base Form 1.2 dm$^3$ of distilled water and then 47 g of the monohydrochloride obtained above are added to a 2-dm$^3$ three-necked flask, the mixture is heated to 55° C. and 30 cm$^3$ of concentrated aqueous ammonia (d=0.925) are poured in and then the mixture is heated to 85° C. in order to promote solubilization. An insoluble matter is filtered while hot on 40 g of Supercel and washed with three times 50 cm$^3$ of boiling water. After concentrating the filtrate to half and another filtration on 10 g of Supercel, 1.2 dm$^3$ of ethanol are added and the mixture is stirred for 5 minutes and then allowed to stand overnight on an ice bath. In the morning, the mixture is filtered, washed with three times 50 cm$^3$ of 66% ethanol and with twice 50 cm$^3$ of ethanol, dried under vacuum at 45° C., and 34.2 g (79%) of crude 2-amino-bis-4,6-[(1'-methyl-4'-amino-6'-quinaldinio)amino]triazine dichloride are obtained. 600 cm$^3$ of distilled water and the 34.2 g of crude base are introduced into a 2-dm$^3$ three-necked flask, with stirring, the mixture is heated at 50° C. until an almost complete dissolution is obtained, and the insoluble matter is filtered. The resulting filtrate is loaded into a 3-dm$^3$ three-necked flask, and 1.4 dm$^3$ of ethanol are rapidly poured in, with stirring. The whitish gelatinous precipitate obtained is filtered, washed with three times 100 cm$^3$ of ethanol, dried under vacuum at 45° C., and 30.7 g (71%) of 2-amino-bis-4,6-[(1'-methyl-4'-amino-6'-quinaldinio)amino]triazine dichloride are obtained in the form of a white solid whose characteristics are the following:

melting point=334° C.; $^1$H NMR spectrum (300 MHz, (CD$_3$)$_2$SO d6, d in ppm): 2.72 (s: 6H); 4.01 (s: 6H); 6.79 (s: 2H); 7.09 (unresolved complex: 2H); 8.11 (d, J=10 Hz: 2H); 8.21 (dd, J=10 and 2 Hz: 2H); from 8.40 to 8.75 (broad unresolved complex: 4H); 9.01 (broad s: 2H); 9.83 (unresolved complex: 2H).

EXAMPLE 2

Preparation of 2-amino-bis-4,6-[(1'-ethyl-4'-amino-6'-quinaldinio)amino]triazine Dichloride 75 cm$^3$ of distilled water are introduced into a 1-dm$^3$ three-necked flask and 16.45 g (0.06 mol) of 1-ethyl-4,6-diaminoquinaldinium chloride hydrochloride, which may be obtained according to U.S. Pat. No. 2,585,905, are loaded, with stirring, and then 300 cm$^3$ of ethanol are poured in. The mixture is heated to 55° C., then 4.95 g (0.03 mol) of 2-amino-4,6-dichlorotriazine are added and the mixture is heated under reflux for 2 and a half hours. The mixture is cooled and left overnight on an ice bath. The precipitate obtained is filtered, washed with 100 cm$^3$ of 80% ethanol and then dried at 45° C. 16.47 g (91%) of 2-amino-bis-4,6-[(1'-ethyl-4'-amino-6'-quinaldinio)amino]triazine dichloride monohydrochloride are thus obtained.

Release and Purification of the Base Form

The 16.47 g of monohydrochloride obtained above are loaded, with stirring, into a 250-cm$^3$ round-bottomed flask containing 200 cm$^3$ of distilled water and 8 cm$^3$ of concentrated aqueous ammonia (d=0.925) are poured in and the mixture is heated to reflux temperature in order to promote solubilization. A light insoluble matter is filtered while hot on Supercel and washed with twice 10 cm$^3$ of boiling water. After concentrating the filtrate to half, 350 cm$^3$ of ethanol are added, with stirring, causing an abundant white precipitate, and the mixture is left overnight on an ice bath. The precipitate is filtered, washed with five times 10 cm$^3$ of 80% ethanol, dried under vacuum at 55° C., and 12.87 g (76%) of 2-amino-bis-4,6-[(1'-ethyl-4'-amino-6'-quinaldinio)amino]triazine dichloride are obtained in the form of a hygroscopic white powder whose characteristics are the following:

melting point=302° C.; $^1$H NMR spectrum (300 MHz, $(CD_3)_2SO$ d6, d in ppm): 1.42 (t, J=7 Hz: 6H); 2.74 (s: 6H); 4.57 (q, J=7 Hz: 4H); 6.80 (s: 2H); 7.09 (unresolved complex: 2H); 8.13 (d, J=10 Hz: 2H); 8.21 (dd, J=10 and 2 Hz: 2H); from 8.40 to 8.75 (broad unresolved complex: 4H); 9.01 (broad s: 2H); 9.83 (unresolved complex: 2H).

EXAMPLE 3

Preparation of 2-Dimethylamino-bis-4,6-[(1'-methyl-4'-amino-61-quinaldinio)amino]triazine Dichloride 60 cm$^3$ of distilled water are introduced into a 1-dm$^3$ three-necked flask and 13.01 g (0.05 mol) of 1-methyl-4,6-diaminoquinaldinium chloride hydrochloride, which may be obtained according to J. Chem. Soc., 1953, 50, are loaded, with stirring. A yellow solution is obtained into which 240 cm$^3$ of ethanol are poured, causing an abundant yellow precipitate. After dissolution by heating to 50° C., 4.83 g (0.025 mol) of 2-dimethylamino-4,6-dichloro-triazine, which may be prepared according to J. Amer. Chem. Soc., 1948, 70, 3726, are added. After a few minutes, a precipitate appears and the mixture is heated under reflux for 1 and a half hours. The mixture is cooled for 1 hour on an ice bath and then the precipitate obtained is filtered, washed with four times 30 cm$^3$ of ethanol and dried. 12.92 g (86%) of 2-dimethylamino-bis-4,6-[(1'-methyl-4'-amino-6'-quinaldinio)amino]triazine dichloride are obtained in the form of a hygroscopic cream-colored powder whose characteristics are the following:

melting point=345° C.; $^1$H NMR spectrum (300 MHz, $(CD_3)_2SO$ d6, d in ppm): 2.72 (s: 6H); 3.18 (s: 6H); 4.00 (s: 6H); 6.75 (s: 2H); 8.12 (d, J=9.5 Hz: 2H); 8.22 (mt: 2H); from 8.40 to 8.65 (broad unresolved complex: 4H); 8.79 (broad s: 2H); 9.83 (unresolved complex: 2H):

EXAMPLE 4

Preparation of 2-Methylamino-bis-4,6-[(4'-amino-6'-quinaldinyl)amino]triazine Trihydrochloride 34 cm$^3$ of distilled water and 126 cm$^3$ of normal hydrochloric acid are introduced into a 2-dm$^3$ three-necked flask and 21.82 g (0.1 mol) of 4,6-diaminoquinaldine, which may be obtained according to J. Chem. Soc., 1953, 50, are loaded, with stirring. 600 cm$^3$ of ethanol are poured into the orange-colored solution obtained and the mixture is heated to 65° C., and then 10.74 g (0.06 mol) of 2-methylamino-4,6-dichlorotriazine, which may be prepared according to Chem. Berichte, 1899, 32, 700, are added and 40 cm$^3$ of ethanol are poured in. A yellow precipitate appears which thickens rapidly on heating under reflux for 2 hours. After cooling overnight on an ice bath, the precipitate obtained is filtered, washed with three times 120 cm$^3$ of 80% ethanol, dried and 27.3 g (81%) of 2-methylamino-bis-4,6-[(4'-amino-6'-quinaldinyl)amino]-triazine trihydrochloride are obtained in the form of a hygroscopic white powder whose characteristics are the following:

melting point=340° C.; $^1$H NMR spectrum (300 MHz, $(CD_3)_2SO$ d6, d in ppm): 2.62 (broad s: 6H); 2.94 (broad s: 3H); 6.64 (broad s: 2H); from 7.60 to 7.80 (broad unresolved complex: 1H); 7.89 (broad d, J=9.5 Hz: 2H); 8.10 (broad d, J=9.5 Hz: 2H); from 8.35 to 8.65 (broad unresolved complex: 4H); from 8.70 to 8.95 (broad unresolved complex: 2H); from 9.80 to 10.00 (broad unresolved complex: 2H); 13.76 (unresolved complex: 2H):

EXAMPLE 5

Preparation of 2-Amino-bis-4,6-[(1'-methyl-6'-quinolinio)amino]triazine Dichloride 225 cm$^3$ of distilled water are introduced into a 2-dm$^3$ three-necked flask and 41.5 g (0.18 mol) of 1-methyl-6-aminoquinolinium chloride hydrochloride, which may be obtained according to Zh.Org.Khim.; 1993, 29(10), 2018, are loaded, with stirring.

A yellow solution is obtained into which 900 cm$^3$ of ethanol are poured, causing an abundant precipitate. After dissolution by heating to 50° C., 14.8 g (0.09 mol) of 2-amino-4,6-dichlorotriazine are added, and the mixture is heated under reflux for 1 hour; a yellow precipitate appears rapidly. The mixture is cooled overnight on an ice bath and then the precipitate obtained is filtered, washed with twice 50 cm$^3$ of ethanol, dried and 36.6 g (79%) of 2-amino-bis-4,6-[(1'-methyl-6'-quinolinio)amino]triazine dichloride monohydrochloride are obtained.

Release and Purification of the Base Form 200 cm$^3$ of distilled water are added to a 1-dm$^3$ three-necked flask and then the 36.6 g of monohydrochloride obtained above are loaded, with stirring, the mixture is heated to 80° C. and 10 cm$^3$ of concentrated aqueous ammonia (d=0.925) are poured in, and an insoluble matter is filtered on Supercel. The preceding filtrate is poured, with stirring, over 5 minutes into a 6-dm$^3$ three-necked flask containing 3 dm$^3$ of ethanol, and a fine bright yellow precipitate appears, which is left for 2 days on an ice bath, then filtered, washed with twice 50 cm$^3$ of ethanol, dried and 19.1 g (44%) of 2-amino-bis-4,6-[(1'-methyl-6'-quinolinio)amino]triazine dichloride are obtained in the form of a hygroscopic yellow powder whose characteristics are the following:

melting point=296° C.; $^1$H NMR spectrum (300 MHz, $(CD_3)_2SO$ d6, d in ppm): 4.64 (s: 6H); 7.11 (unresolved complex: 2H); 8.10 (dd, J=8.5 and 6 Hz: 2H); 8.46 (d, J=10 Hz: 2H); 8.56 (dd, J=10 and 2 Hz: 2H); 9.17 (broad d, J=8.5 Hz: 2H); 9.30 (mt: 4H); 10.26 (unresolved complex: 2H).

EXAMPLE 6

Preparation of 2-Methylamino-bis-4,6-[(4'-methylamino-6'-quinaldinyl)amino]triazine Dichloride Trihydrochloride Step A: Preparation of 4-Methylamino-6-aminoguinaldine 240 cm$^3$ of acetic acid are introduced into a 2-dm$^3$ three-necked flask and 57.4 g (0.25 mol) of 6-acetamido-4-methoxyquinaldine, prepared according to J. Amer. Chem. Soc., 1948, 70, 4065, are loaded, with stirring. Methylamine is bubbled, with stirring, until saturation is obtained, and then the mixture is heated under reflux for 2 hours. The mixture is cooled, and the preceding operation is again carried out, the mixture is cooled, and the solution obtained is poured, with stirring, into a 2-dm$^3$ three-necked flask containing 300 cm$^3$ of distilled water and 470 cm$^3$ of normal hydrochloric acid. The mixture is then heated at 100° C. for 11 hours and then it is left overnight on an ice bath. The crystallized product is filtered, giving 25 g of hydrochloride, the mother liquors are concentrated, left overnight on an ice bath and then filtered to give again 150 g of hydrochloride. The 175 g of hydrochloride are taken up in 300 cm³ of distilled water and dissolved by heating to 50° C., treated with 1 g of charcoal and filtered on Supercel. The filtrate is heated to 90° C. and alkalinized by addition of 54 cm³ of concentrated sodium hydroxide. The precipitate obtained by cooling overnight on an ice bath is washed with four times 100 cm³ of distilled water, dried and 33 g (70%) of 4-methylamino-6-amino-quinaldine are obtained.

Step B 25 cm³ of distilled water and 101 cm³ of normal hydrochloric acid are introduced into a 2-dm³ three-necked flask, and 18.9 g (0.101 mol) of 4-methylamino-6-aminoquinaldine are loaded, the orange-colored solution obtained is heated to 75° C., and then 500 cm³ of ethanol are poured in over 2 minutes, and the 8.59 g (0.048 mol) of 2-methylamino-4,6-dichlorotriazine, prepared according to Example 4, are added all at once. After 5 minutes, a precipitate appears and the mixture is heated under reflux for 2 hours, allowed to cool, with stirring, for 3 hours and abandoned for 8 days on an ice bath. The precipitate obtained is filtered, washed with twice 100 cm³ of 80% ethanol and with three times 100 cm³ of ethanol, dried and 21.7 g (77%) of 2-methylamino-bis-4,6-[(4'-methylamino-6'-quinaldinyl)amino]triazine dichloride trihydrochloride are obtained in the form of a hygroscopic cream-colored powder whose characteristics are the following:

melting point=355° C.; $^1$H NMR spectrum (300 MHz, $(CD_3)_2SO$ d6, d in ppm): 2.68 (s: 6H); 2.93 (s: 3H); 3.04 (unresolved complex: 6H); 6.59 (s: 2H); from 7.40 to 7.70 (broad unresolved complex: 1H); 7.88 (d, J=9 Hz: 2H); 8.08 (broad d, J=9 Hz: 2H); from 8.50 to 8.95 (broad unresolved complex; 2H); from 8.75 to 8.95 (unresolved complex: 2H); from 9.70 to 10.10 (broad unresolved complex: 2H); 13.79 (unresolved complex: 2H).

EXAMPLE 7

Preparation of 2-Amino-bis-4,6-[(9'-amino-10'-methyl-2'-acridinio)amino]triazine Dichloride Hydrochloride Step A: Preparation of 2-Acetamido-9-amino-acridine 72 cm³ of acetic acid are introduced into a 250-cm³ three-necked flask and 12 g (0.0575 mol) of 2,9-diaminoacridine, prepared according to J. Chem. Soc., 1949, 1148, are loaded, with stirring, and then 4.1 cm³ (0.0575 mol) of acetyl chloride are poured in. The temperature rises to 50° C. and the solution forms into a mass. The mixture is maintained at 60° C. for 1 hour, cooled and diluted with 200 cm³ of diethyl ether. 15.2 g of hydrochloride are obtained by filtration. 2 dm³ of distilled water are introduced into a 4-dm³ round-bottomed flask and the 15.2 g of hydrochloride are loaded, with stirring. The mixture is heated to reflux temperature, filtered and alkalinized with aqueous ammonia. The base crystallizes, is filtered and dried. 11.2 g (78%) of 2-acetamido-9-aminoacridine are obtained.

Step B: Preparation of 2-Acetamido-9-amino-10-methylacridinium Sulphate 300 cm³ of nitrobenzene are introduced into a 1-dm³ three-necked flask and then 11.2 g (0.0446 mol) of 2-acetamido-9-aminoacridine and 11 cm³ (0.116 mol) of dimethyl sulphate are successively introduced, with stirring. The mixture is then heated at 140° C. for 20 minutes. After cooling, the precipitate obtained is filtered, washed with 20 cm³ of nitrobenzene and six times 20 cm³ of diethyl ether, air-dried and 14.35 g (85%) of 2-acetamido-9-amino-10-methylacridinium sulphate are obtained.

Step C: Preparation of 2-Acetamido-9-amino-10-methylacridinium Chloride Hydrochloride 600 cm³ of distilled water are introduced into a 2-dm³ round-bottomed flask and 13 g of 2-acetamido-9-amino-10-methylacridinium sulphate (0.0344 mol) are loaded, with stirring, the mixture is heated to reflux temperature until almost complete dissolution has been obtained and the insoluble matter is filtered. After cooling, 900 cm³ of a 35% aqueous sodium chloride solution are poured in, the mixture is allowed to precipitate and filtered. 20 cm³ of concentrated hydrochloric acid (d=1.18) are introduced into a 100-cm³ round-bottomed flask and the preceding compound is loaded and heated under reflux for 5 minutes, diluted with 67 cm³ of ethanol and allowed to crystallize on ice. The crystals formed are filtered, washed with twice 5 cm³ of ethanol and with three times 10 cm³ of diethyl ether, dried and 5.1 g (50%) of 2-acetamido-9-amino-10-methylacridinium chloride hydrochloride are obtained.

Step D 5 cm³ of distilled water and 37 cm³ of ethanol are introduced into a 100-cm³ three-necked flask and 1 g (0.00338 mol) of 2-acetamido-9-amino-10-methylacridinium chloride hydrochloride is loaded, with stirring, and the mixture is heated to 80° C. and 0.28 g (0.0017 mol) of 2-amino-4,6-dichlorotriazine is added. After 5 minutes, a precipitate appears and the mixture is heated under reflux for 2 hours and then allowed to cool, filtered, washed with three times 3 cm³ of ethanol and with 5 cm³ of ether, dried under vacuum and 0.8 g (73%) of 2-amino-bis-4,6-[(9'-amino-10'-methyl-2'-acridinio)amino]triazine dichloride hydrochloride is obtained in the form of a hygroscopic yellow ochre-colored powder whose characteristic is the following:

melting point=310° C.

EXAMPLE 8

Preparation of 2-Amino-bis-4,6-[(4'-amino-6'-quinaldinyl)amino]triazine Trihydrochloride (the corresponding base is also called SURFENE C)

5.25 dm³ of distilled water are introduced into a 10-dm³ three-necked flask and 368.4 g (2.127 mol) of 4,6-diaminoquinaldine, prepared according to Example 4, are loaded, with stirring, and then 117 g (0.709 mol) of 2-amino-4,6-dichlorotriazine, prepared according to Example 1, are added. A yellow precipitate forms immediately and the mixture is heated under reflux for 2 hours. After cooling and acidifying to pH=3.4 by addition of 1.3 dm³ of normal hydrochloric acid, the mixture is heated under reflux for 15 minutes, 20 g of charcoal are added and the reflux is maintained for 10 minutes and then the mixture is filtered. The preceding solution is introduced into a 10-dm³ three-necked flask and heated to 80° C., and then 852 cm³ of hydrochloric acid (d=1.19) are poured in over 30 minutes. At the end of the pouring, a pale yellow precipitate appears which, after cooling on an ice bath, is filtered, washed with four times 250 cm³ of a hydrochloric acid solution composed of 250 cm³ of hydrochloric acid (d=1.19) and 2 dm³ of distilled water, and then dried under vacuum at 60° C. and 385.4 g (99%) of trihydrochloride are obtained. 1.9 dm$^3$ of ethanol are introduced into a 4-dm$^3$ three-necked flask and the preceding 385.4 g are loaded, with stirring for 5 hours at room temperature protected from light, the mixture is filtered, then washed with twice 250 cm$^3$ of ethanol and dried; 346 g (89%) of 2-amino-bis-4,6-[(4'-amino-6'-quinaldinyl)amino]triazine trihydrochloride are obtained in the form of a hygroscopic cream-colored powder whose characteristic is the following:

melting point=345° C.

EXAMPLE 9

2-Amino-bis-4,6-(p-amidinoanilino)triazine Trihydrochloride

This product may be obtained according to J. Chem. Soc., 1960, 4525, in the form of a hygroscopic cream-colored powder.

EXAMPLE 10

Preparation of 2-Methylthio-bis-4,6-[(1'-methyl-4'-amino-6'-quinaldinio)amino]triazine Dichloride 60 cm$^3$ of distilled water are introduced into a 1-dm$^3$ three-necked flask and 13.01 g (0.05 mol) of 1-methyl-4,6-diaminoquinaldinium chloride hydrochloride, which may be obtained according to J. Chem. Soc., 1953, 50, are loaded, with stirring. A yellow solution is obtained into which 240 cm$^3$ of ethanol are poured, causing an abundant yellow precipitate. After dissolution by heating to 50° C., 4.90 g (0.025 mol) of 2-methylthio-4,6-dichlorotriazine, which may be prepared according to Ang. Chem. Int. Ed., 1966, 5, 960, are added. After a few minutes, a precipitate appears and the mixture is heated under reflux for one and a half hours. The mixture is cooled overnight on an ice bath, then the precipitate obtained is filtered, washed with four times 30 cm$^3$ of ethanol and dried. 10.70 g (75%) of 2-methylthio-bis-4,6-[(1'-methyl-4'-amino-6'-quinaldinio)amino]triazine dichloride are obtained in the form of a hygroscopic cream-colored powder whose characteristic is the following:

melting point=320° C.

EXAMPLE 11

Preparation of 2-Chloro-bis-4,6-[(4'-dimethylamino-6'-quinaldinyl)amino]triazine Dihydrochloride Dihydrate Step A : Preparation of 4-dimethylamino-6-aminoguinaldine The procedure is carried out as in Step A of Example 6, but starting with 57.4 g (0.25 mol) of 6-acetamido-4-methoxyquinaldine, prepared according to J. Amer. Chem. Soc., 1948, 70, 4065, and 100 cm$^3$ of a 40% aqueous dimethylamine solution in 250 cm$^3$ of acetic acid heated at 100° C. for 2 hours in a 1-dm$^3$ autoclave. 38.71 g (77%) of 4-dimethylamino-6-aminoquinaldine are then obtained, after acid-base purification, on carrying out the procedure as in Step A of Example 6.

Step B 402 mg (2 mmol) of 4-dimethylamino-6-aminoquinaldine are dissolved in 7 cm$^3$ of acetic acid in a 25-cm$^3$ three-necked flask, and then 184 mg (1 mmol) of cyanuryl chloride are added over 2 minutes and then the mixture is heated at 90° C. for 3 hours. After cooling, the crystals formed are dewatered, washed with 2.5 cm$^3$ of acetic acid and dried under vacuum at 100° C. 588 mg (94%) of 2-chloro-bis-4,6-[(4'-dimethylamino-6'-quinaldinyl)amino] triazine dihydrochloride dihydrate are thus obtained in the form of pale yellow crystals whose characteristics are the following:

melting point=350° C.; elemental analysis: % C=51.75 (calc=52.06); % H=5.67 (calc=5.50); % N=19.98 (calc=20.23).

EXAMPLE 12

Preparation of 2-Methylthio-bis-4,6-[(41-dimethylamino-6'-quinaldinyl)amino]triazine Hydrate Step A: Preparation of 4-dimethylamino-6-aminoquinaldine The procedure is carried out as in Step A of Example 6, but starting with 57.4 g (0.25 mol) of 6-acetamido-4-methoxyquinaldine, prepared according to J. Amer. Chem. Soc., 1948, 70, 4065, and 100 cm$^3$ of a 40% aqueous dimethylamine solution in 250 cm$^3$ of acetic acid heated at 100° C. for 2 hours in a 1-dm$^3$ autoclave. 38.71 g (77%) of 4-dimethylamino-6-aminoquinaldine are then obtained, after acid-base purification, on carrying out the procedure as in Step A of Example 6.

Step B 100 cm$^3$ of 90% aqueous ethanol are introduced into a 250-cm$^3$ three-necked flask and 4.02 g (0.02 mol) of 4-dimethylamino-6-aminoquinaldine and 1.96 g (0.01 mol) of 2-methylthio-4,6-dichlorotriazine, which may be prepared according to Ang. Chem. Int. Ed., 1966, 5, 960, are loaded, with stirring. After a few minutes, a precipitate appears and the mixture is heated under reflux for 1 and a half hours. The mixture is cooled overnight on an ice bath and then the precipitate obtained is filtered and washed with four times 30 cm$^3$ of ethanol and dried. 5.26 g (88%) of crude hydrochloride are obtained.

75 cm$^3$ of 90% aqueous ethanol are added to a 250-cm$^3$ three-necked flask and then the 5.26 g of hydrochloride previously obtained are loaded, with stirring, the mixture is heated to 80° C. and 5 cm$^3$ of concentrated aqueous ammonia (d=0.925) are poured in, and the mixture is allowed to crystallize for 2 days on an ice bath. The mixture is filtered, washed with twice 5 cm$^3$ of 90% aqueous ethanol, dried and 3.20 g (59.5%) of 2-methylthio-bis-4,6-[(4'-dimethylamino-6'-quinaldinyl)amino]triazine hydrate are obtained in the form of a pale yellow solid whose characteristics are the following:

melting point=280–30° C.; elemental analysis: % C=62.06 (calc=62.48); % H=5.81 (calc=62.48); % N=23.80 (calc=23.42).

EXAMPLE 13

Preparation of N,N'-(4-amino-6-guinaldinyl)-urea Dihydrochloride (the corresponding base, also called SURFENE, may be prepared according to Ang. Chem 1939, 891)

400 cm$^3$ of distilled water are introduced into a 500-cm$^3$ three-necked flask and 30 g (0.2 mol) of 4,6-diaminoquinaldine, which may be prepared according to J. Chem. Soc., 1953, 50, are loaded, with stirring, and then 8.4 g (0.06 mol) of sodium acetate trihydrate are added and the mixture is heated to 95–96° C. A stream of phosgene is then caused to pass through until saturation is obtained (5 to 10 minutes), and then the mixture is maintained at 95–96° C. for 1 hour. After cooling and acidifying by addition of 200 cm$^3$ of 6 N hydrochloric acid, the precipitate formed is dewatered, washed with 200 cm$^3$ of N hydrochloric acid and dried under vacuum at 60° C., and 30 g of crude hydrochloride are thus obtained, which hydrochloride is recrystallized from 300 cm$^3$ of distilled water and 30 cm$^3$ of concentrated hydrochloric acid in the presence of charcoal. After cooling, the crystals formed are dewatered, washed with N hydrochloric acid, and then with acetone and dried under vacuum at 40° C. 27 g (60.5%) of N,N'-(4-amino-6-quinaldinyl)urea dihydrochloride are thus obtained in the form of a hygroscopic cream-colored powder whose characteristic is the following:

melting point=329–40° C.

EXAMPLE 14

Preparation of N$^1$,N$^5$-bis(7-chloro-1-methyl-4-quinolinio)pentane-1,5-diamine Diiodide 3 g (7 mmol) of N$^1$,N$^5$-bis(7-chloroquinolin-4-yl)pentane-1,5-diamine, which may be prepared according to J. Med. Chem. 1992, 35, 2129, are dissolved, by heating to around 50° C., in 60 cm$^3$ of butan-2-one. 3 g (21 mmol) of methyl iodide are added and the mixture is heated under reflux for 5 hours. The crystals formed are dewatered, washed with butan-2-one and then with diethyl ether and dried under vacuum. 3 g (60%) of N$^1$,N$^5$-bis(7-chloro-1-methyl-4-quinolinio)-pentane-1,5-diamine diiodide are thus obtained in the form of beige crystals whose characteristic is the following:

melting point=277–78° C.

EXAMPLE 15

Preparation of bis-2,4-[(4'-Amino-6'-quinaldinyl)amino]pyrimidine Trihydrochloride Pentahydrate 1.73 g (10 mmol) of 4,6-diamino-1-methylquinoline, which may be obtained according to J. Chem. Soc., 1953, 50, and 0.74 g of 2,4-dichloropyrimidine in 75 cm$^3$ of ethanol and 5 cm$^3$ of water are heated for 5 hours under reflux in a 250-cm$^3$ three-necked flask. The reaction medium is concentrated by half and then allowed to crystallize on an ice bath overnight. The precipitate formed is dewatered, washed with ethanol and then with diethyl ether and dried under vacuum. The precipitate obtained is stirred for 6 hours in 10 cm$^3$ of 0.2 N hydrochloric acid and then dewatered, washed with water and dried under vacuum at 80° C. 0.98 g (46.5%) of bis-2,4-[(4'-amino-6'-quinaldinyl)amino]pyrimidine trihydrochloride pentahydrate is thus obtained in the form of a yellow solid whose characteristics are the following:

melting point=310–20° C.; elemental analysis: % C=47.37 (calc=47.46); % H=5.51 (calc=5.67); % N=18.41 (calc=18.45); % Cl=15.84 (calc=15.76)

EXAMPLE 16

Preparation of 1,5-(4'-Amino-6'-quinaldinyl)-biguanide Trihydrochloride Dihydrate 5 cm$^3$ of water, 3 cm$^3$ of 5N hydrochloric acid, 1.3 g (7.5 mmol) of 4,6-diaminoquinaldine, which may be obtained according to J. Chem. Soc., 1953, 50, and 0.34 g (3.75 mmol) of sodium dicyanamide are added to a 25-cm$^3$ three-necked flask and the mixture is heated at 50–55° C. overnight. After cooling, the precipitate formed is dewatered, washed with ice-cold water and dried under vacuum at 70° C. 0.47 g (22.5%) of 1,5-(4'-amino-6'-quinaldinyl)biguanide trihydrochloride dihydrate is thus obtained in the form of yellow crystals whose characteristics are the following:

melting point=262–66° C.; elemental analysis: % C=47.85 (calc=47.56); % H=5.67 (calc=5.38); % N=22.96 (calc=22.69); % Cl=18.79 (calc=19.14).

EXAMPLE 17

The G-quartet, antitelomerase and cytotoxic activities of the various compounds exemplified are determined according to the operating protocols described above.

| EXAMPLE | FLUORESCENCE Tm (° C.) | TRAP IC50 ($\mu$M) | Cytotox. A549 IC50 ($\mu$M) |
|---|---|---|---|
| 1 | — | 0.25 | 0.59/1.9* |
| 2 | 48° | 0.056 | 4.7 |
| 3 | 52° | 0.22 | — |
| 4 | 48° | 0.51 | 3.1 |
| 5 | 57° | 0.13 | 0.56/1.8* |
| 6 | 44° | 0.3 | 1.9 |
| 7 | 55° | 0.89 | 4.9 |
| 8 | — | 0.051 | 9.1 |
| 9 | — | 0.74 | 0.53 |
| 10 | — | 0.24 | 3.6 |
| 11 | 57° | 3 | 5.14 |
| 12 | 70° | 0.041 | 0.44/1.1* |
| 13 | — | 0.72 | — |
| 14 | — | 1.4/4.9* | 6.5 |
| 15 | 53° | 0.49 | 8.7 |
| 16 | 52° | 2/4.5* | 5.8 |

-continued

| | A | Ar₁ | R₃ | Ar₂ | R'₃ | G4 Tm °C. | TRAP IC₅₀ μM | Cytotox. A549 IC₅₀ μM |
|---|---|---|---|---|---|---|---|---|
| 17-1 | SMe | 4-amino-2-methylquinoline | H | 4-amino-2-methylquinoline | H | 57 | 0.049 | 1.6 |
| 17-2 | SMe | ClH, 4-imino-1,2-dimethylquinoline | H | ClH, 4-imino-1,2-dimethylquinoline | H | | 0.95 | 6.1 |
| 17-3 | SMe | 4-methoxy-2-methylquinoline | H | 4-methoxy-2-methylquinoline | H | | 3.9 | 3.2 |
| 18-1 | SMe | 4-amino-2-methylquinoline | H | quinoline | Me | 47 | 3.5 | |
| 18-2 | SMe | 4-amino-2-methylquinoline | H | 4-methoxy-2-methylquinoline | H | 49 | 2.3 | |
| 18-3 | SMe | 4-amino-2-methylquinoline | H | 4-(dimethylamino)-2-methylquinoline | H | 57 | 0.34 | 10 |
| 18-4 | SMe | 4-amino-2-methylquinoline | H | 2,4-dimethylquinoline | H | 50 | 2.2 | |
| 18-5 | SMe | 4-amino-2-methylquinoline | H | quinoline | H | 47 | 3.4 | |

-continued
| | | | | | | | | |
|---|---|---|---|---|---|---|---|---|
| 18-6 | SMe | 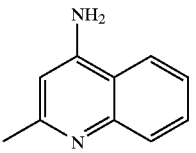 | H | 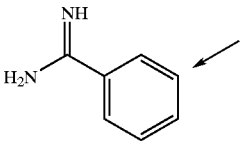 | H | 50 | 2.6 | 10 |
| 18-7 | SMe | 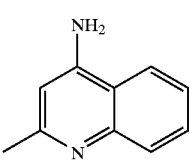 | H | 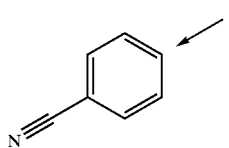 | H | 51 | 3.3 | 8 |
| 18-8 | SMe | 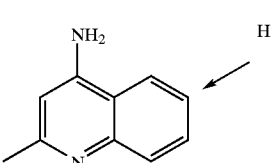 | H | 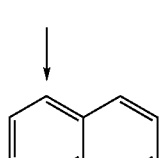 | H | 49 | 3.4 | |
| 18-9 | SMe | 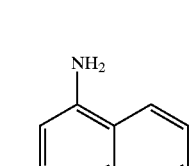 | H | 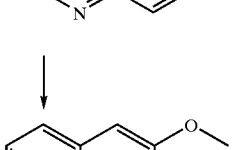 | H | 51 | 3.4 | 9.5 |
| 18-10 | SMe | 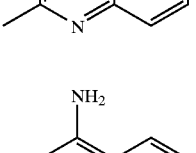 | H | 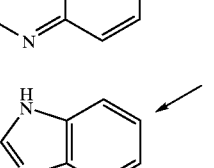 | H | 49 | 3.3 | 10 |
| 18-11 | SMe | 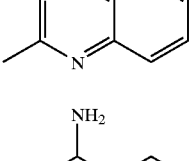 | H | 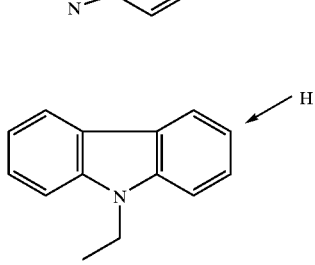 | H | 48 | 3.3 | 1.3 |
| 18-12 | SMe | 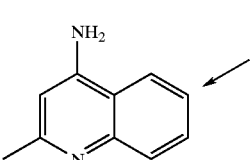 | H | 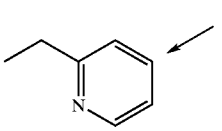 | H | | 2.8 | |
| 18-13 | SMe | 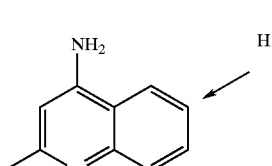 | H | 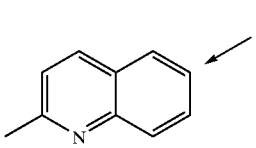 | H | | 3.4 | |
| 19-1 | N(Et)$_2$ | 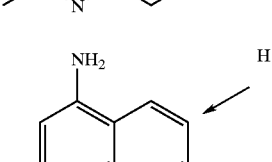 | H | 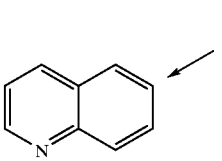 | H | 58 | 1.0 | 1.5 |

-continued

| 19-2 | N(Et)₂ | 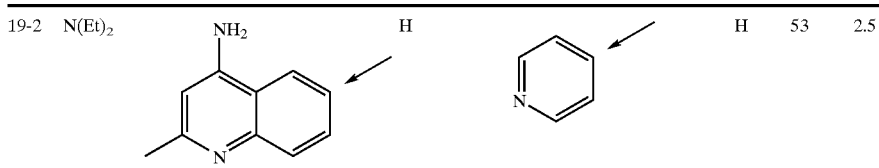 | H | | H | 53 | 2.5 |

*results of two independent experiments

What is claimed is:

1. Compounds which bind the G-quadruplex structure of the telomers, characterized in that they correspond to the following general formula:

nitrogen-containing aromatic ring —NR₃— distribution agent —NR'₃— aromatic ring in which
nitrogen-containing aromatic ring represents:
a quinoline optionally substituted with at least one group in which Ra and Rb, which are identical or different, represent a short-chain C1–C4 alkyl, alkoxy radical,
a quinoline possessing a nitrogen atom in quaternary form,
a benzamidine, or
a pyridine
the aromatic ring represents
a quinoline optionally substituted with at least one group N(Ra) (Rb) in which Ra and Rb, which are identical or different, represent hydrogen, a short-chain C1–C4 alkyl, alkoxy radical,
a quinoline possessing a nitrogen atom quaternary form,
a benzamidine,
a pyridine,
a phenyl ring optionally substituted at the meta or para position with a halogen group, C1–C4 alkoxy group, cyano group, carbonylamino group optionally substituted with one or more C1–C4 alkyl groups, guanyl groups, C1–C4 alkylthio groups, amino groups, C1–C4 alkylamino groups, C1–C4 dialkylamino groups for each alkyl group, nitro group, alkylene-amino group or alkenyleneamino group, or
a mono- or bi- or tricyclic hetero-cyclic ring comprising 0 to 2 heteroatoms per ring provided that at least one heteroatom is present in at least one ring optionally substituted with one or more C1–C4 alkyl groups, or with alkylene or alkenylene groups
R3 and R'3, which are identical or different, represent independently of one another hydrogen or a C1–C4 alkyl radical
the distribution agent represents:
a triazine group optionally substituted with an alkyl radical having 1 to 4 carbon atoms, a thio, oxy or amino radical which are themselves optionally substituted with one or more short-chain alkyl chains containing 1 to 4 carbon atoms or a halogen atom
or one of its salts
with the proviso that the compound is not (a) benzenecarboximidamide,4-[4-chloro-6-(phenylamino)-1,3,5-triazin-2-yl]amino, or (b) 1,3,5-triazine-2,4,6-triamine,N,N'-bis(4-amino-2-methyl-6-quinolinyl)-trihydrochloride.

2. Compounds according to claim 1, characterized in that they correspond to formula (I) below:

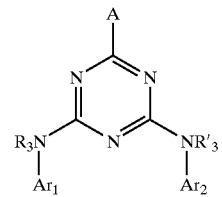

in which:
A represents
an amino group of formula NR1R2 in which R1 and R2, which are identical or different, represent hydrogen or a straight or branched alkyl group containing 1 to 4 carbon atoms or
a group OR1 or SR1 in which R1 has the same meaning as above or
an alkyl group containing 1 to 4 carbon atoms or a trifluoromethyl group or
a hydrogen atom or
a halogen atom chosen from fluorine, chlorine, bromine or iodine
R3 and R'3, which are identical or different, represent independently of one another hydrogen or a C1–C4 alkyl group
Ar₁ and Ar₂, which are identical or different, represent
1. when Ar₁ and Ar₂ are identical:
a quinoline motif optionally substituted with at least one group N(Ra)(Rb) in which Ra and Rb, which are identical or different, represent hydrogen or a short-chain alkyl and/or alkoxy radical containing 1 to 4 carbon atoms or
a quinoline possessing a nitrogen atom in quaternary form or
a benzamidine or
a pyridine attached at the 4-position or fused with an aryl or heteroaryl group optionally substituted with a C1–C4 alkyl group
2. when Ar₁ and Ar₂ are different
Ar₁ and Ar₂ both represent one of the possibilities mentioned above for Ar₁ and Ar₂ or
Ar₁ represents one of the above possibilities and Ar₂ represents
a phenyl ring optionally substituted at the meta or para position with a halogen group, C1–C4 alkoxy group, cyano group, carbonylamino group optionally substituted with one or more C1–C4 alkyl groups, guanyl groups, C1–C4 alkylthio groups, amino groups, C1–C4 alkylamino groups, C1–C4 dialkylamino groups for each alkyl group, nitro group, alkyleneamino group or alkenyleneamino group
a mono- or bi- or tricyclic hetero-cyclic ring comprising 0 to 2 heteroatoms per ring provided that at least one heteroatom is present in at least one ring optionally substituted with one or more C1–C4 alkyl groups or with alkylene or alkenylene groups or one of its salts.

3. Compounds according to claim 2, characterized in that Ar$_1$ and Ar$_2$ represent a group chosen from the following groups: 4-amino- or 4-methyamino- or 4-dimethylamino-quinolyl or -quinolinium in which the quinolinium ring is optionally substituted with a methyl group.

4. Compounds according to claim 2, characterized in that the groups R1 and R2 represent the methylthio, amino, alkylamino or dialkylamino radical, in which radicals the alkyl groups possess 1 to 4 carbon atoms.

5. Compounds according to claim 2, characterized in that A represents a methylthio group.

6. Compounds corresponding to the following formula (I):

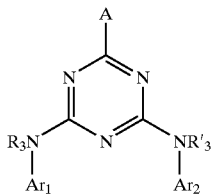

in which:

A represents
   an amino group of formula NR1 R2 in which R1 and R2, which are identical or different, represent hydrogen or a straight or branched alkyl group containing 1 to 4 carbon atoms,
   a group OR1 or SR1 in which R1 has the same meaning as above,
   an alkyl group containing 1 to 4 carbon atoms or a trifluoromethyl group,
   a hydrogen atom, or
   a halogen atom chosen from fluorine, chlorine, bromine or iodine R3 and R'3, which are identical or different, represent independently of one another a hydrogen atom or a C1–C4 alkyl group Ar$_1$ and Ar$_2$, which are identical or different, represent
1. when Art and Ar$_2$ are identical:
   a quinoline motif optionally substituted with at least one group N(Ra)(Rb) in which Ra and Rb, which are identical or different, represent hydrogen, or a short-chain alkyl, alkoxy radical containing 1 to 4 carbon atoms,
   a quinoline possessing a nitrogen atom in quaternary form,
   a benzamidine except in the case where A represents diethylamine, hydrogen or an amine group, or
   a pyridine attached at the 4-position or fused with an aryl or heteroaryl group optionally substituted with a C1–C4 alkyl group
2. when Ar$_1$ and Ar$_2$ are different
   Ar$_1$ and Ar$_2$ both represent one of the possibilities mentioned above for Ar$_1$ and Ar$_2$ or
   Ar$_1$ represents one of the above possibilities and Ar$_2$ represents
      a phenyl ring optionally substituted at the meta or para position with a halogen group, C1–C4 alkoxy group, cyano group, carbonylamino group optionally substituted with one or more C1–C4 alkyl groups, guanyl groups, C1–C4 alkylthio groups, amino groups, C1–C4 alkylamino groups, C1–C4 dialkylamino groups for each alkyl group, nitro group, alkyleneamino group, or alkenyleneamino group
      a mono- or bi- or tricyclic hetero-cyclic ring comprising 0 to 2 heteroatoms per ring provided that at least one heteroatom is present in at least one ring optionally substituted with one or more C1–C4 alkyl groups or with alkylene or alkenylene groups or one or its salts
excluding 2-amino-bis-4,6-[(4'-amino-6'-quinaldinyl)amino]triazine dihydrochloride and 2-amino-bis-4,6-(p-amidinoanilino) triazine dihydrochloride; and with the proviso that the compound is not (a) benzenecarboximidamide,4-[4-chloro-6-(phenylamino)-1,3, 5-triazin-2-yl]amino, or (b) 1,3,5-triazine-2,4,6-triamine,N, N'-bis(4-amino-2-methyl-6- quinolinyl)-trihydrochloride.

7. Compounds according to claim 6, characterized in that when Ar$_1$ and Ar$_2$ are identical, Ar$_1$ and Ar$_2$ represent a group chosen from 4-amino- or 4-methylamino- or 4-dimethylamino-quinolyl or -quinolinium groups in which the quinolinium ring is optionally substituted with a methyl group.

8. Compounds according to claim 6, characterized in that R1 and R2 represent hydrogen.

9. Compounds according to claim 6, characterized in that A represents a methylthio group.

10. Compounds according to claim 6, characterized in that when Ar$_1$ and Ar$_2$ are different
   1. Ar$_1$ represents:
      a quinoline motif substituted with at least one group N(Ra)(Rb) in which Ra and Rb, which are identical or different, represent hydrogen or a short-chain alkyl or alkoxy radical containing 1 to 4 carbon atoms and/or
      a quinoline possessing a nitrogen atom in quaternary form or
      a benzamidine except in the case where A represents diethylamine, hydrogen or an amine group or
      a pyridine attached at the 4-position or fused with an aryl or heteroaryl group
   2. Ar$_2$ represents
      a ring as defined above but different or
      a phenyl ring optionally substituted at the meta or para position with a halogen, methoxy, cyano, carbonylamino, guanyl, methylthio, amino, methylamino, dimethylamino, morpholine, alkyleneamino or alkenyleneamino group
      a quinoline, benzimidazole, indole, benzothiophene, benzofuran, benzothiazol, benzoxazol, carbazol, quinazoline or quinoxaline ring optionally substituted with one or more C1–C4 alkyl groups or with alkylene or alkenylene groups or one of its salts excluding 2-amino-bis-4,6-[(4'-amino-6'-quinaldinyl)amino]triazine dihydro-chloride and 2-amino-bis-4,6-(p-amidinoanilino)-triazine.

11. Compounds according to claim 6, chosen from:
   2-amino-bis-4,6-[(1'-methyl-4'-amino-6'-quinaldinio)amino]triazine dichloride
   2-amino-bis-4,6-[(1'-ethyl-4'-amino-6'-quinaldinio)amino]triazine dichloride
   2-dimethylamino-bis-4,6-[(1'-methyl-4'-amino-6'-quinaldinio)amino]triazine dichloride
   2-methylamino-bis-4,6-[(4'-amino-6'-quinaldinyl)amino]triazine trihydrochloride
   2-amino-bis-4,6-[(1'-methyl-6'-quinolinio)-amino]triazine dichloride 2-methylamino-bis-4,6-[(4'-methylamino-6'-quinaldinyl)
 amino]triazine dichloride trihydrochloride
2-amino-bis-4,6-[(9'-amino-10'-methyl-2'-acridinio)
 amino]triazine dichloride hydrochloride
2-methylthio-bis-4,6-[(1'-methyl4'-amino-6'-quinaldinio)
 amino]triazine dichloride
2-chloro-bis-4,6-[(4'-dimethylamino-6'-quinaldinyl)
 amino]triazine dihydrochloride dihydrate
2-methylthio-bis-4,6-[(4'-dimethylamino-6'-quinaidinyl)
 amino]triazine hydrate.

12. Compounds according to claim 11 chosen from:
2-methylthio-bis-4,6-[(4'-dimethylamino-6'-quinaldinyl)
 amino]triazine hydrate
2-chloro-bis-4,6-[(4'-dimethylamino-6'-quinaldinyl)
 amino]triazine dihydrochloride dihydrate
6-[4-(4-amino-2-methylquinolin-6-ylamino)-6-
 methylsulphanyl-[1,3,5]triazin-2-ylamino]-2-methyl-
 quinolin-4-ol
N6-[4-(4-dimethylamino-2-methylquinolin-6-ylamino)-
 6-methylsulphanyl-[1,3,5]triazin-2-yl]-2-
 methylquinoline-4,6-diamine
N6-[4-(4-amino-2-methylquinolin-6-ylamino)-6-
 methylsulphanyl-[1,3,5]triazin-2-yl]-2-methyl-
 quinoline-4,6-diamine
N6-[4-(4-methoxy-2-methylquinolin-6-ylamino)-6-
 methylsulphanyl-[1,3,5]triazin-2-yl]-4-methoxy-2-
 methylquinolin-6-amine.

13. A pharmaceutical composition comprising one or more compounds of claim 6, and a pharmaceutically acceptable carrier.

14. Therapeutic combinations consisting of a compound according to claim 1 and another anticancer compound.

15. Combinations according to claim 14, characterized in that the anticancer compound is chosen from alkylating agents, platinum derivatives, antibiotic agents, antimicrotubule agents, anthracyclines, group I and II topoisomerases, fluoropyrimidines, cytidine analogues, adenosine analogues, various enzymes and compounds such as L-asparaginase, hydroxyurea, trans-retinoic acid, suramine, irinotecan, topotecan, dexrazoxane, amifostine, herceptin as well as oestrogenic and androgenic hormones.

16. Therapeutic combination consisting of the administration of a compound according to claim 1 and the administration of radiation.

17. Combinations according to any one of claims 14 to 16, characterized in that each of the compounds or treatments is administered simultaneously, separately or sequentially.

18. A method of inhibiting telomerase activity, comprising administering a therapeutically effective amount of one or more compounds of claim 1 to a patient, wherein the level of telomerase activity in the patient following the administration is reduced relative to the level of telomerase activity existing prior to the administration.

19. A method of treating a cancer, comprising administering a therapeutically effective amount of one or more compounds of claim 1 to a patient in need of such a treatment, wherein the level of telomerase activity following the administration is reduced relative to the level of telomerase activity existing prior to the administration.

* * * * *